(12) United States Patent
Cabiri

(10) Patent No.: US 10,688,243 B2
(45) Date of Patent: *Jun. 23, 2020

(54) CARTRIDGE INSERTION ASSEMBLY

(71) Applicant: West Pharma. Services IL, Ltd., Ra'anana (IL)

(72) Inventor: Oz Cabiri, Macabim-Reut (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/395,166

(22) Filed: Dec. 30, 2016

(65) Prior Publication Data

US 2017/0106138 A1 Apr. 20, 2017

Related U.S. Application Data

(63) Continuation of application No. 13/892,905, filed on May 13, 2013, now Pat. No. 9,572,926, which is a
(Continued)

(51) Int. Cl.
*A61M 5/145* (2006.01)
*A61M 5/142* (2006.01)
(Continued)

(52) U.S. Cl.
CPC ...... *A61M 5/1456* (2013.01); *A61M 5/14248* (2013.01); *A61M 5/158* (2013.01);
(Continued)

(58) Field of Classification Search
CPC ............. A61M 5/142; A61M 5/14244; A61M 5/14248; A61M 5/145; A61M 5/14546;
(Continued)

(56) References Cited

U.S. PATENT DOCUMENTS

| 4,300,554 A | 11/1981 | Hessberg et al. |
|---|---|---|
| 4,689,043 A | 8/1987 | Bisha |

(Continued)

FOREIGN PATENT DOCUMENTS

| CN | 1408443 A | 4/2003 |
|---|---|---|
| CN | 101239205 A | 8/2008 |

(Continued)

OTHER PUBLICATIONS

Office Action dated Jul. 13, 2011 in U.S. Appl. No. 12/559,563 by Cabiri.

(Continued)

*Primary Examiner* — Lauren P Farrar
*Assistant Examiner* — James D Ponton
(74) *Attorney, Agent, or Firm* — Panitch Schwarze Belisario & Nadel LLP

(57) ABSTRACT

A cartridge insertion assembly including apparatus with a pathway formed therein, a cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed position, the door coupling element couples the cartridge coupling element with a coupling element of the activation mechanism.

11 Claims, 11 Drawing Sheets

Related U.S. Application Data continuation of application No. 13/272,555, filed on Oct. 13, 2011, now Pat. No. 8,465,455, which is a continuation of application No. 12/559,563, filed on Sep. 15, 2009, now Pat. No. 8,157,769.

(51) Int. Cl.
*A61M 5/158* (2006.01)
*A61M 5/162* (2006.01)

(52) U.S. Cl.
CPC ... *A61M 5/162* (2013.01); *A61M 2005/14268* (2013.01); *A61M 2005/14573* (2013.01)

(58) Field of Classification Search
CPC ............ A61M 5/1456; A61M 5/14566; A61M 5/1458; A61M 2005/14573
See application file for complete search history.

(56) References Cited

U.S. PATENT DOCUMENTS

| | | |
|---|---|---|
| 5,090,877 A | 2/1992 | D'Silva |
| 5,364,364 A | 11/1994 | Kasvikis et al. |
| 5,445,621 A | 8/1995 | Poli et al. |
| 5,505,709 A | 4/1996 | Funderburk et al. |
| D372,098 S | 7/1996 | Lattin et al. |
| D384,745 S | 10/1997 | Lattin et al. |
| 5,779,676 A | 7/1998 | Kriesel et al. |
| 5,820,406 A | 10/1998 | Hetherington |
| 5,830,187 A | 11/1998 | Kriesel et al. |
| 5,858,001 A | 1/1999 | Tsals et al. |
| 5,954,697 A | 9/1999 | Srisathapat et al. |
| 6,117,575 A | 9/2000 | Dinsdale |
| 6,160,487 A | 12/2000 | DeLuca |
| 6,305,908 B1 | 10/2001 | Hermann et al. |
| 6,423,036 B1 | 7/2002 | Van Huizen |
| 6,599,272 B1 | 7/2003 | Hjertman et al. |
| 7,569,050 B2 | 8/2009 | Moberg et al. |
| 7,588,559 B2 | 9/2009 | Aravena et al. |
| D602,155 S | 10/2009 | Foley et al. |
| 7,749,194 B2 | 7/2010 | Edwards et al. |
| 7,806,868 B2 | 10/2010 | De Polo et al. |
| 7,967,795 B1 | 6/2011 | Cabiri |
| 8,157,769 B2 | 4/2012 | Cabiri |
| D685,083 S | 6/2013 | Schneider et al. |
| 8,465,455 B2 | 6/2013 | Cabiri |
| D687,141 S | 7/2013 | Schneider et al. |
| D687,536 S | 8/2013 | Guarraia et al. |
| D723,157 S | 2/2015 | Clemente et al. |
| D768,288 S | 10/2016 | O'Connor et al. |
| D774,640 S | 12/2016 | Tyce et al. |
| D776,262 S | 1/2017 | Tyce et al. |
| D776,263 S | 1/2017 | Tyce et al. |
| D776,264 S | 1/2017 | Tyce et al. |
| D776,265 S | 1/2017 | Tyce et al. |
| 9,707,335 B2 | 7/2017 | Agard et al. |
| D794,776 S | 8/2017 | Tyce et al. |
| 9,737,655 B2 | 8/2017 | Clemente et al. |
| 9,782,545 B2 | 10/2017 | Gross et al. |
| 9,802,030 B2 | 10/2017 | Clemente et al. |
| D804,019 S | 11/2017 | Costello et al. |
| 9,814,832 B2 | 11/2017 | Agard et al. |
| D804,650 S | 12/2017 | Costello et al. |
| D805,186 S | 12/2017 | Costello et al. |
| D805,187 S | 12/2017 | Costello et al. |
| D805,188 S | 12/2017 | Costello et al. |
| D805,189 S | 12/2017 | Costello et al. |
| D805,190 S | 12/2017 | Costello et al. |
| 9,861,759 B2 | 1/2018 | Gross et al. |
| D810,278 S | 2/2018 | Cabiri et al. |
| D810,279 S | 2/2018 | Cabiri et al. |
| D811,583 S | 2/2018 | Cabiri et al. |
| D811,584 S | 2/2018 | Cabiri et al. |
| 2003/0109827 A1 | 6/2003 | Lavi et al. |
| 2004/0015131 A1 | 1/2004 | Flaherty et al. |
| 2004/0064088 A1 | 4/2004 | Gorman et al. |
| 2005/0203461 A1 | 9/2005 | Flaherty et al. |
| 2006/0264831 A1 | 11/2006 | Skwarek et al. |
| 2007/0167912 A1 | 7/2007 | Causey et al. |
| 2007/0197968 A1* | 8/2007 | Pongpairochana ..... A61M 5/20 604/131 |
| 2007/0219480 A1 | 9/2007 | Kamen et al. |
| 2008/0097381 A1 | 4/2008 | Moberg et al. |
| 2008/0234627 A1 | 9/2008 | Dent et al. |
| 2008/0255516 A1* | 10/2008 | Yodfat ............... A61M 5/14248 604/151 |
| 2008/0281270 A1 | 11/2008 | Cross et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0131860 A1* | 5/2009 | Nielsen ............. A61M 5/14248 604/66 |
| 2009/0143735 A1 | 6/2009 | De Polo et al. |
| 2009/0243234 A1 | 10/2009 | Sharifi |
| 2010/0081993 A1* | 4/2010 | O'Connor ......... A61M 5/14248 604/151 |
| 2010/0168683 A1 | 7/2010 | Cabiri |
| 2010/0211011 A1 | 8/2010 | Haar |
| 2011/0066131 A1 | 3/2011 | Cabiri |
| 2011/0137239 A1 | 6/2011 | DeBelser et al. |
| 2012/0035546 A1 | 2/2012 | Cabiri |
| 2013/0060233 A1 | 3/2013 | O'Connor et al. |
| 2013/0296792 A1 | 11/2013 | Cabiri |
| 2014/0188073 A1 | 7/2014 | Cabiri et al. |
| 2015/0057613 A1 | 2/2015 | Clemente et al. |
| 2016/0058941 A1 | 3/2016 | Wu et al. |
| 2016/0256352 A1 | 9/2016 | Bar-El et al. |
| 2017/0028132 A1 | 2/2017 | Cronenberg et al. |
| 2017/0106138 A1 | 4/2017 | Cabiri |
| 2017/0224915 A1 | 8/2017 | Destefano et al. |
| 2017/0281859 A1 | 10/2017 | Agard et al. |
| 2017/0312450 A1 | 11/2017 | Gross et al. |
| 2017/0354781 A1 | 12/2017 | Cronenberg et al. |
| 2017/0354782 A1 | 12/2017 | Quinn et al. |
| 2017/0354783 A1 | 12/2017 | Gazeley et al. |
| 2017/0354785 A1 | 12/2017 | Gazeley et al. |
| 2017/0354788 A1 | 12/2017 | Quinn et al. |
| 2018/0001073 A1 | 1/2018 | Clemente et al. |
| 2018/0008769 A1 | 1/2018 | O'Connor et al. |
| 2018/0021508 A1 | 1/2018 | Destefano et al. |
| 2018/0028747 A1 | 2/2018 | Hanson et al. |
| 2018/0043091 A1 | 2/2018 | Agard et al. |

FOREIGN PATENT DOCUMENTS

| | | |
|---|---|---|
| EP | 2698180 A1 | 2/2014 |
| EP | 2727617 A1 | 5/2014 |
| WO | 2009044401 A2 | 4/2009 |
| WO | 2011/034799 A1 | 3/2011 |
| WO | 2012032411 A2 | 3/2012 |
| WO | 2012160157 A1 | 11/2012 |
| WO | 2012160160 A1 | 11/2012 |
| WO | 2014/107408 A1 | 7/2014 |

OTHER PUBLICATIONS

Office Action dated Jul. 2, 2012 in U.S. Appl. No. No. 13/272,555 by Cabiri.
Office Action dated Jan. 4, 2016 in U.S. Appl. No. No. 13/892,905 by Cabiri.
Int'l Search Report and Written Opinion dated Dec. 1, 2011 in Int'l Application No. PCT/US2010/048556.
Int'l Preliminary Report on Patentability dated Jan. 9, 2011 in Int'l Application No. PCT/US2010/048556.
Office Action dated Sep. 29, 2013 in CN Application No. 201080040968.7.
Office Action dated Apr. 24, 2013 in CN Application No. 201080040968.7.
Search Report dated Apr. 24, 2013 in CN Application No. 201080040968.7.
Office Action dated Jul. 29, 2013 in JP Application No. 2012-529808.

(56) References Cited

OTHER PUBLICATIONS

Office Action dated Dec. 17, 2013 in JP Application No. 2012-529808.
Office Action dated Nov. 16, 2015 in U.S. Appl. No. 13/733,516 by Cabiri.
Int'l Search Report and Written Opinion dated Apr. 3, 2014 in Int'l Application No. PCT/US2013/078040.
Int'l Preliminary Report on Patentability dated Jul. 16, 2015 in Int'l Application No. PCT/US2013/078040.
U.S. Appl. No. 15/196,775 by Cabiri, filed Jun. 29, 2016.
Office Action dated Jul. 7, 2016 in U.S. Appl. No. 13/892,905 by Cabiri.
Office Action dated Aug. 13, 2018 in IN Application No. 857/KOLNP/2012.
Office Action dated Mar. 15, 2018 in U.S. Appl. No. 29/628,592 by Cabiri.

* cited by examiner

CARTRIDGE INSERTION ASSEMBLY

CROSS-REFERENCE TO RELATED APPLICATIONS

The present application is a continuation of U.S. patent application Ser. No. 13/892,905, filed May 13, 2013 and entitled CARTRIDGE INSERTION ASSEMBLY, which is a continuation of U.S. patent application Ser. No. 13/272,555, filed Oct. 13, 2011 and entitled CARTRIDGE INSERTION ASSEMBLY FOR DRUG DELIVERY SYSTEM and issued as U.S. Pat. No. 8,465,455, which is a continuation of U.S. patent application Ser. No. 12/559,563, filed on Sep. 15, 2009 and entitled "CARTRIDGE INSERTION ASSEMBLY FOR DRUG DELIVERY SYSTEM and issued as U.S. Pat. No. 8,157,769.

The contents of all of the above applications are incorporated by reference in their entireties as if fully set forth herein.

BACKGROUND OF THE INVENTION

The present invention generally relates to drug delivery systems, e.g., external drug pumps, and particularly to an assembly for inserting a cartridge, which contains a substance to be administered to a patient, into the drug delivery system.

External drug pumps are typically used to deliver to patients substances which contain large molecules which cannot be digested when administered orally, such as insulin. Typically, the pump is adhered to the abdomen or chest or other of the patient and delivers the substance to the patient via a cannula that is inserted into the patient subcutaneously, although the invention described below is not limited to needle administration of substances.

BRIEF SUMMARY OF THE INVENTION

The present invention seeks to provide an improved assembly for inserting a cartridge, which contains a substance to be administered to a patient, into a drug pump (or any kind of drug delivery system), as is described more in detail hereinbelow. It is noted that the term "cartridge" encompasses any kind of reservoir or container (disposable or not) for a substance that is to be administered to a patient, such as but not limited to, a vial, ampoule, bottle, pre-filled syringe and the like, and is not limited to any size or shape.

There is thus provided in accordance with an embodiment of the present invention a cartridge insertion assembly including apparatus with a pathway formed therein, a cartridge insertable into the pathway, the cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed position, the door coupling element couples the cartridge coupling element with a coupling element of the activation mechanism.

In accordance with an embodiment of the present invention a locking latch is cantilevered from a base of the apparatus, wherein when the cartridge is fully inserted in the apparatus, the locking latch abuts against a rim of the cartridge, thereby locking the cartridge in the pathway.

In accordance with an embodiment of the present invention when the cartridge is fully inserted in the apparatus, the cartridge abuts against a cartridge stopper disposed in the apparatus.

In accordance with an embodiment of the present invention the cartridge includes a septum at an end opposite to the cartridge coupling element, and the apparatus includes a hollow needle, wherein when the cartridge is fully inserted in the apparatus, the needle punctures the septum.

In accordance with an embodiment of the present invention the door includes a closure member on an inside surface thereof, the closure member including one or more inclined ramp members, wherein closing the door causes the ramp members to slide and push against the cartridge coupling element so as to push the cartridge fully into the apparatus.

In accordance with an embodiment of the present invention the door is formed with one or more ribs, which when the door is fully closed, the ribs are received in one or more corresponding grooves formed in the apparatus.

In accordance with an embodiment of the present invention the closure member includes a hub, wherein when the door is fully closed, the hub is fixedly received in a snap member.

BRIEF DESCRIPTION OF THE SEVERAL VIEWS OF THE DRAWINGS

The present invention will be understood and appreciated more fully from the following detailed description taken in conjunction with the drawings in which.

DETAILED DESCRIPTION OF THE INVENTION

Figure 1:
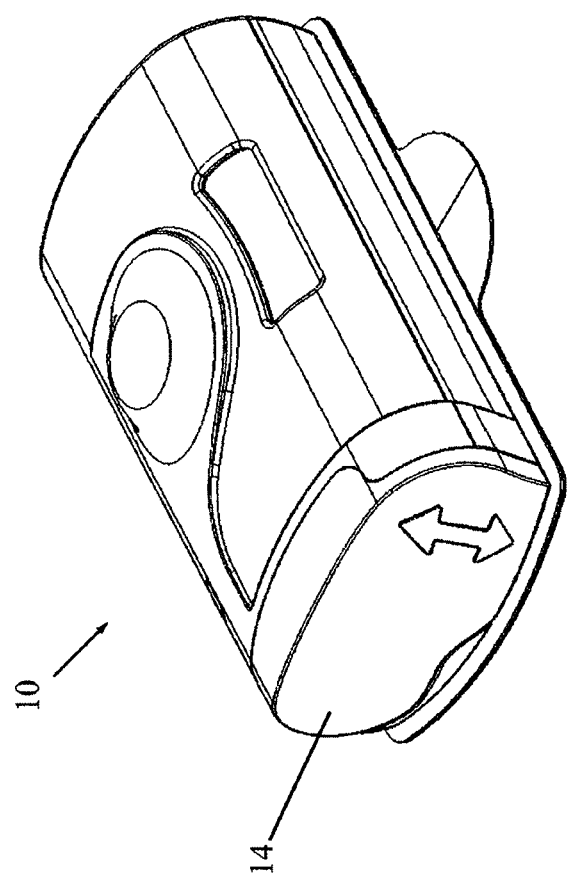
FIG. 1 is a simplified illustration of apparatus for administering a substance to a subject, in accordance with an embodiment of the present invention.
Figure 2:
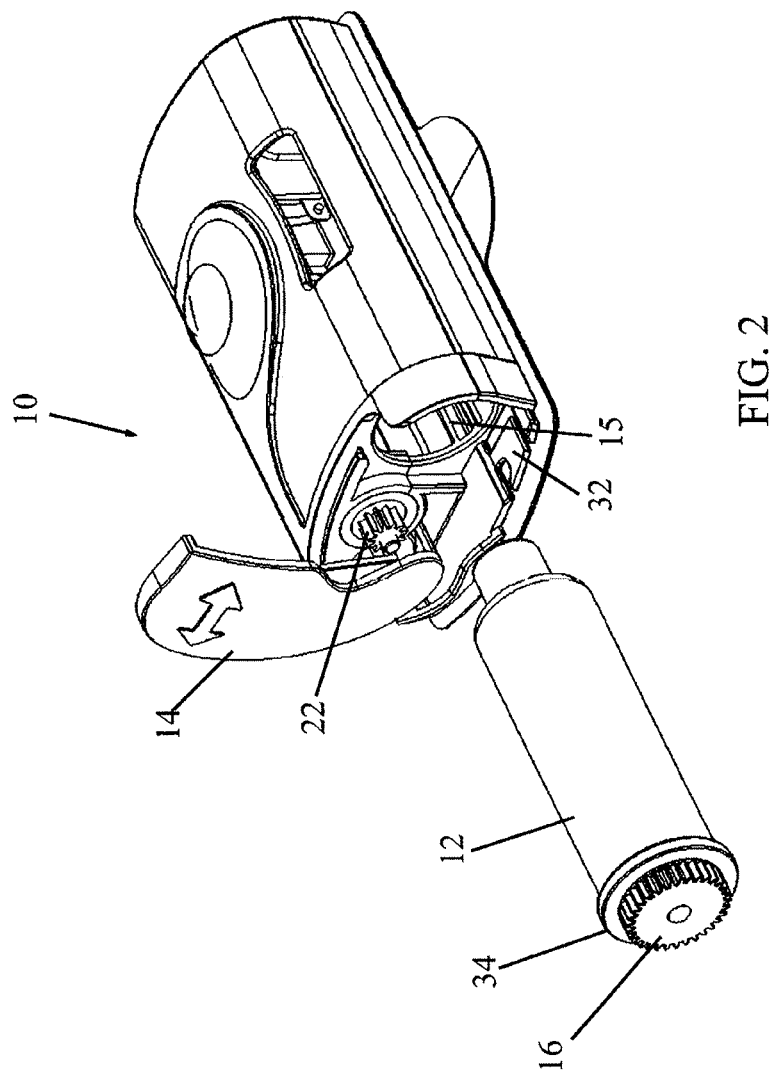
FIG. 2 is a simplified illustration of the apparatus of FIG. 1, showing a door of a cartridge insertion assembly in the open position and a cartridge poised for insertion into the apparatus.

Reference is now made to FIGS. 1 and 2, which illustrate apparatus 10 for administering a substance (e.g., insulin) to a subject, in accordance with a non-limiting embodiment of the present invention. Typically, apparatus 10 includes a cartridge 12 (FIG. 2) that contains the substance to be administered to a subject. FIG. 2 illustrates a door 14 of a cartridge insertion assembly in the open position and cartridge 12 poised for insertion into a pathway 15 in apparatus 10.

As seen in FIG. 2, cartridge 12 includes a cartridge coupling element 16 (e.g., a gear) for coupling (e.g., meshing) with an activation mechanism 18 (seen in FIG. 4, which typically includes a motor, a battery and a control unit) that causes the substance contained in cartridge 12 to be metered out of cartridge 12 for eventual administration to the patient. (In some embodiments, cartridge coupling element 16 is assembled to an end of a driving screw.) The way in which the activation mechanism works to meter the substance out of cartridge 12 is not pertinent to this invention. By way of example, the activation mechanism may work as in an external drug pump of the type described in US Patent Applications 20090093792 and 20090093793 or PCT Patent Application PCT/IL2008/001312 (published as WO 2009/044401), the disclosures of which are incorporated herein by reference. However, the invention is not limited to such a drug pump, and may be used for any kind of suitable administration of substances, not just by needle puncture into the patient, but also transdermally (wherein the substance is metered by apparatus 10 to a transdermal patch), by spray (wherein the substance is metered by apparatus 10 to a spray nozzle), micro needles array and others.

It is noted that although cartridge 12 is typically a one-use item, the electronics, batteries and motor and other elements of the system can be used more than once if desired.

Figure 3:
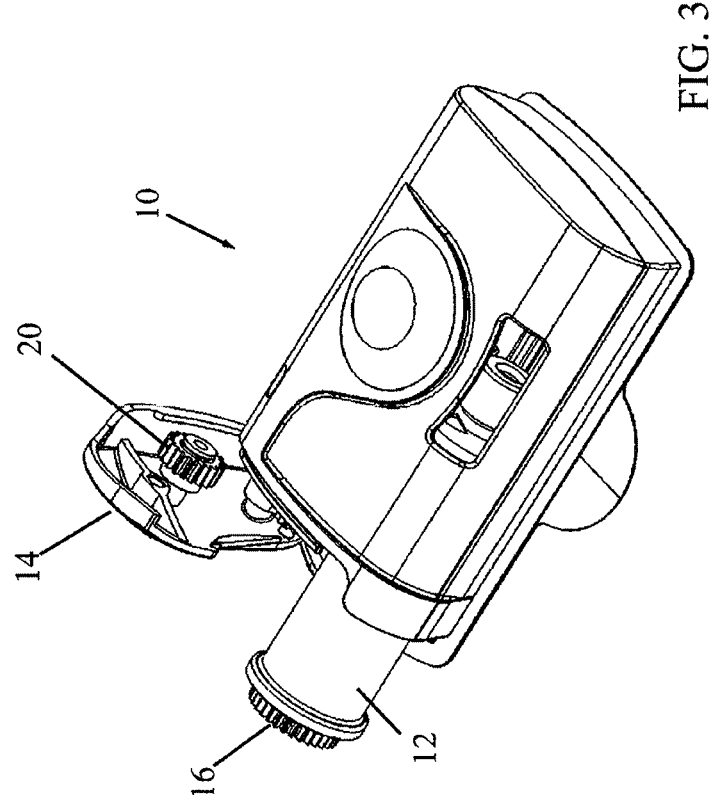
FIG. 3 is a simplified illustration of the cartridge partially inserted into the apparatus.

As seen in FIG. 3, in accordance with a non-limiting embodiment of the present invention, door 14 includes a door coupling element 20 (e.g., a gear, but could also be any other coupling element for transmitting rotary motion, such as a friction wheel) for effecting coupling (e.g., meshing) between the cartridge coupling element 16 and a coupling element 22 (FIG. 2) of the activation mechanism 18, as will be described more in detail below.

Figure 4:
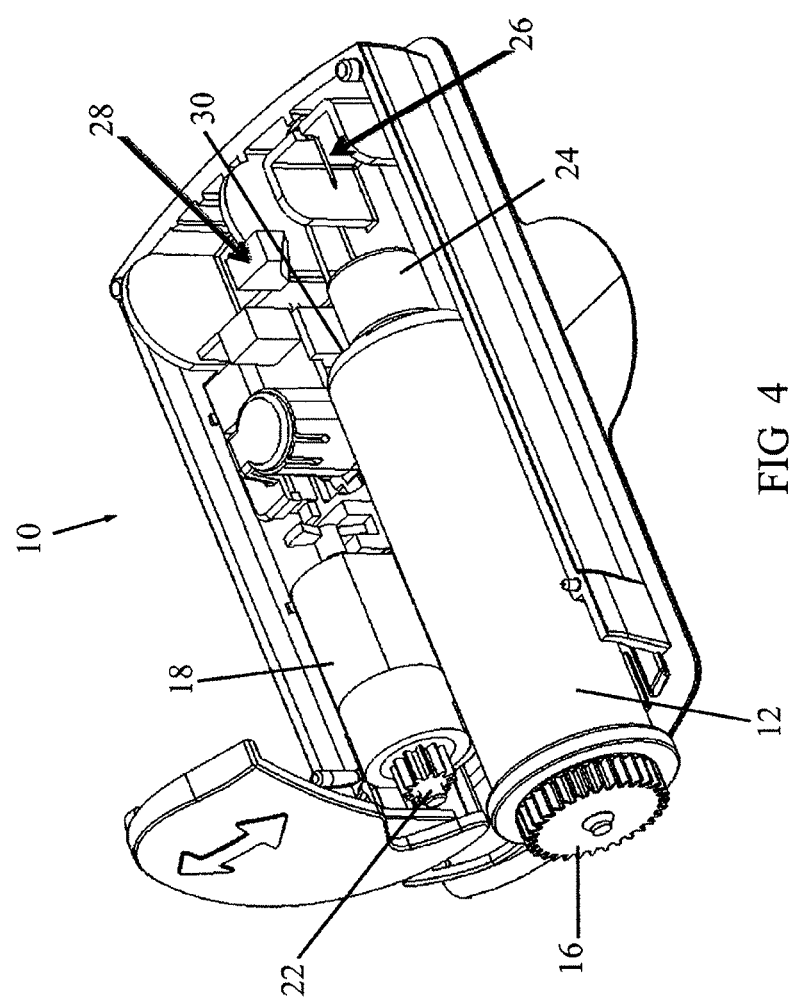
FIG. 4 is a simplified illustration of the cartridge partially inserted into the apparatus, showing components of the cartridge insertion assembly.
Figure 5:
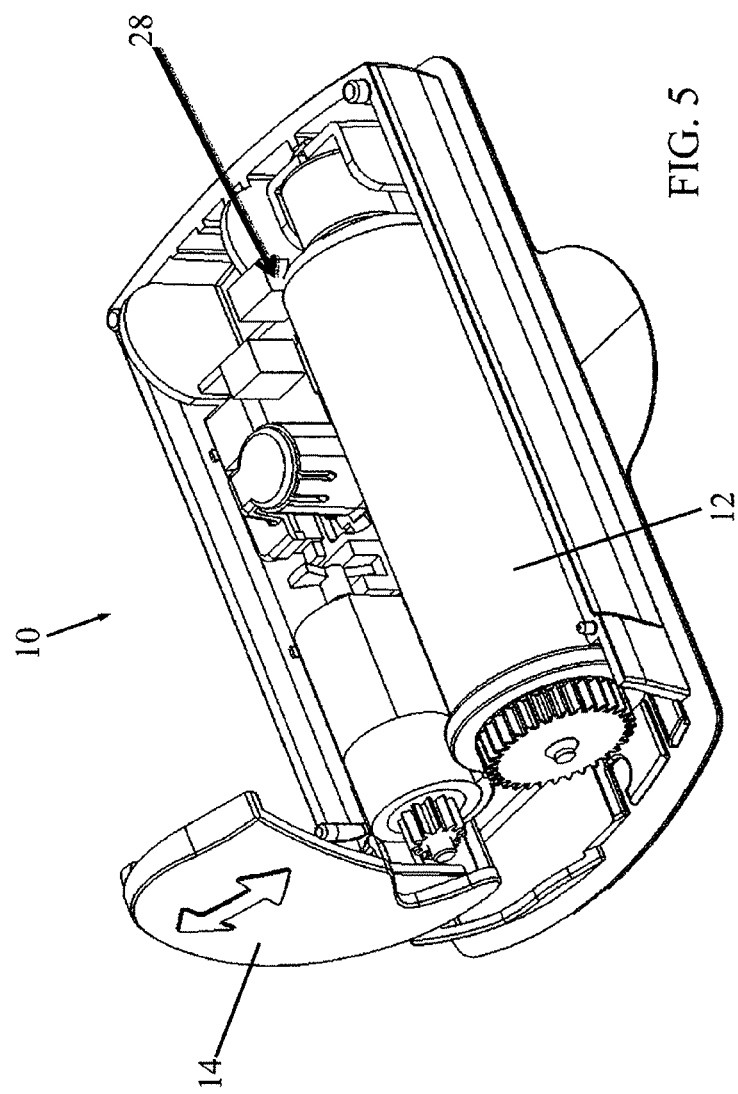
FIG. 5 is a simplified illustration of the cartridge fully inserted into the apparatus up to a cartridge stopper of the cartridge insertion assembly, with the door still open.

Reference is now made to FIG. 4, which illustrates the cartridge 12 partially inserted into apparatus 10, showing components of the cartridge insertion assembly. Cartridge 12 has a septum 24 at an end opposite to cartridge coupling element 16. The septum 24 is pierced by a hollow needle 26 so that contents of cartridge 12 flow out of cartridge 12 into needle 26 and from needle 26 to an exit port (not shown) for eventual administration to the patient. A cartridge stopper 28, which may be made of a rigid material (e.g., plastic) or more preferably a resilient material (e.g., an elastomer or silicone), is provided for arresting movement of cartridge 12 during insertion into apparatus 10 and preventing overinsertion of cartridge 12. Cartridge stopper 28 also prevents the torque, which is generated by the activation mechanism 18 to rotate the driving screw of the cartridge, from rotating cartridge 12. The cartridge stopper 28 abuts against a shoulder 30 of cartridge 12. FIG. 5 shows cartridge 12 fully inserted into apparatus 10 up to cartridge stopper 28 with door 14 still open.

Figure 6:
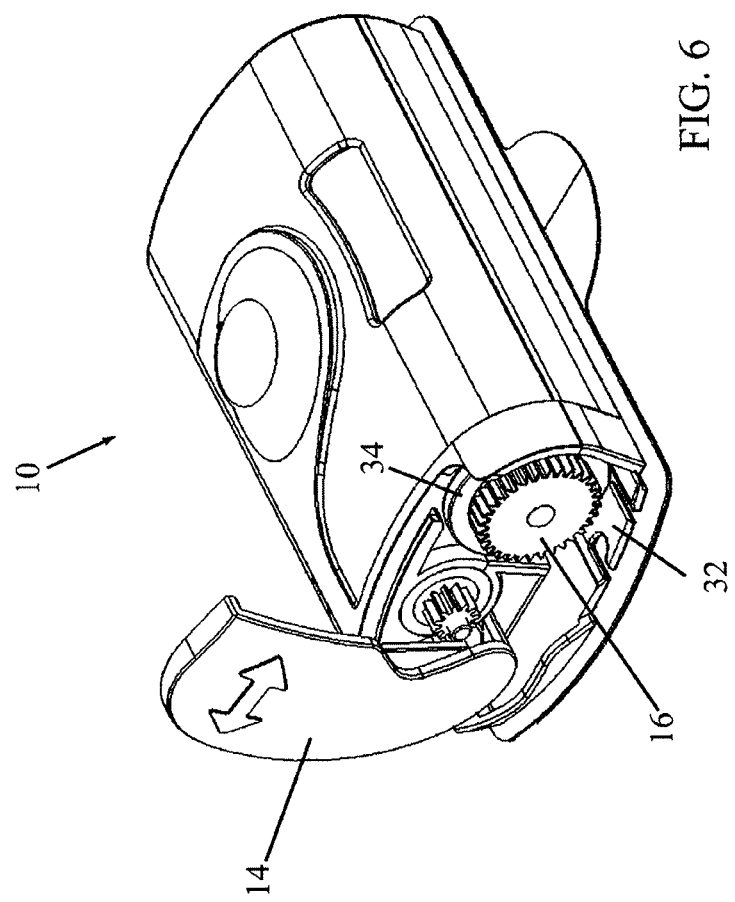
FIG. 6 is a simplified illustration of the cartridge fully inserted into the apparatus and locked in place.
Figure 7:
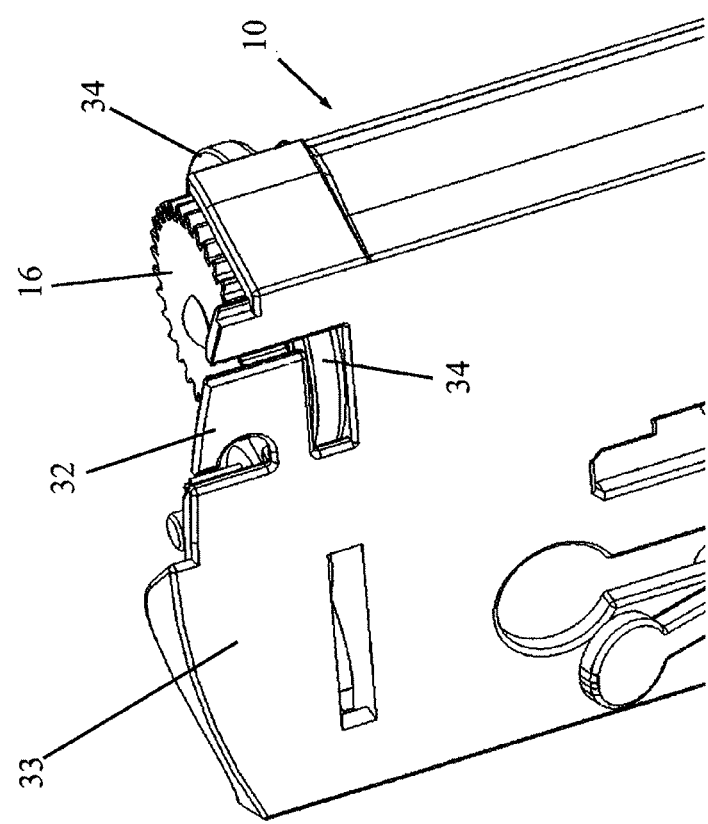
FIG. 7 is a simplified illustration of a locking latch that locks the cartridge in place.

Reference is now made to FIGS. 6 and 7. The cartridge insertion assembly of apparatus 10 includes a locking latch 32 which is cantilevered from a base 33 (FIG. 7) of the apparatus 10. While inserting cartridge 12 into apparatus 10, a rim 34 near cartridge coupling element 16 depresses and slides over locking latch 32. When cartridge 12 is fully inserted into apparatus 10, rim 34 moves past locking latch 32 and locking latch 32 springs back and abuts against rim 34, thereby locking cartridge 12 in place. The user cannot remove cartridge 12 from apparatus 10.

Figure 8:
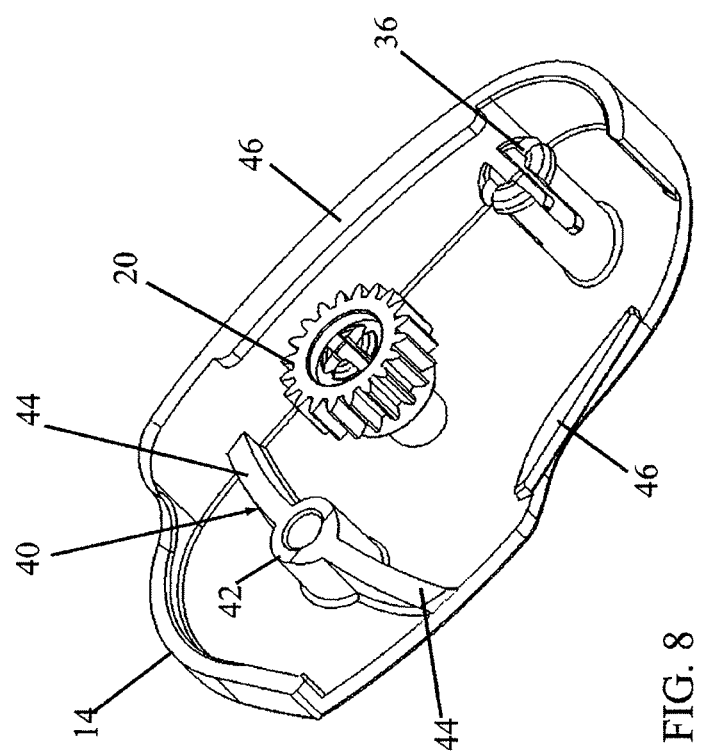
FIG. 8 is a simplified illustration of the inside of the door of the cartridge insertion assembly.
Figure 9:
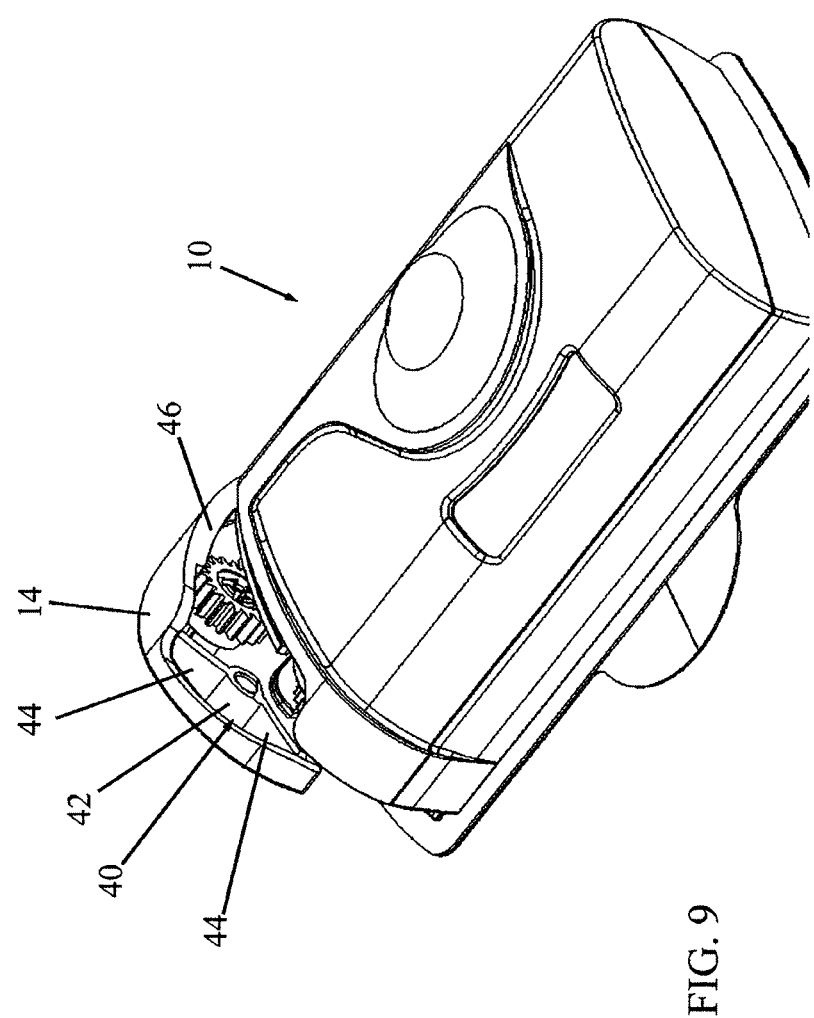
FIG. 9 is a simplified illustration of partially closing the door of the cartridge insertion assembly.

Reference is now made to FIG. 8, which illustrates the inside of door 14. The door coupling element 20 mentioned above is in the middle of the inside of door 14. On one side of element 20 is a hinge member 36 that pivotally connects (e.g., by snap fit) into a corresponding socket 38 (seen in FIG. 10) in the body of apparatus 10. On the other side of element 20 is a closure member 40, which is formed with a central hub 42 and one or more ramp members 44 (in the illustrated embodiment, two inclined ramp members 44 extend on either side of hub 42). Even if the user has not fully inserted cartridge 12 into apparatus 10, the act of closing door 14 (see FIG. 9) causes the ramp members 44 to slide and swipe against cartridge coupling element 16. The inclined surfaces of ramp members 44 gently push and wedge cartridge coupling element 16 to seat fully into apparatus 10 so that septum 24 is pierced by hollow needle 26 as described above with reference to FIGS. 4 and 5.

After the cartridge 12 is locked in place, ramp members 44 keep pushing against the driving screw to create priming of the drug pump, wherein contents of the cartridge 12 overflow and pressurize into the needle 26 and drip out therefrom. This priming process reduces the breaking force (the initial force to remove the plunger after a long storage time) and removes air bubbles from the fluid path.

The inside of door 14 is formed with one or more ribs 46, which when door 14 is fully closed, are received in one or more corresponding grooves 48 (FIG. 10) formed at the end of the housing of apparatus 10. Ribs 46 seated in grooves 48 provide resistance to axial pull-out forces that may be acting on cartridge 12 and door 14 during operation of apparatus 10.

Figure 10:
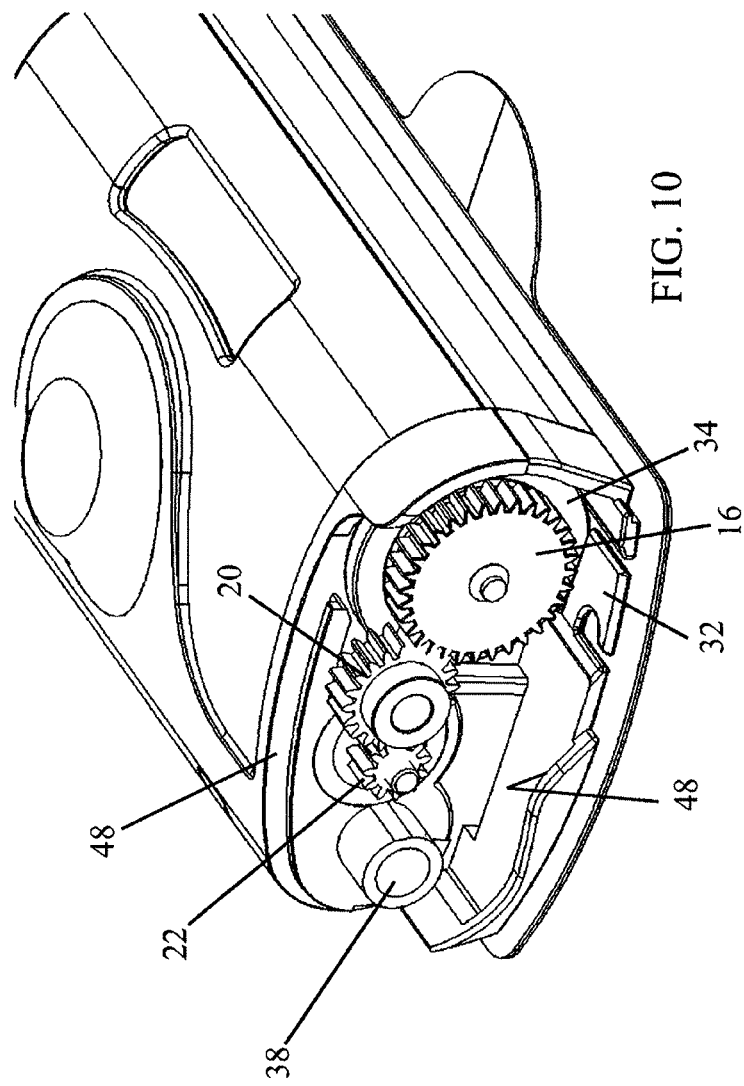
FIG. 10 is a simplified illustration of the door fully closed, but only showing the inner components of the door (e.g., coupling elements) and not the outside surface of the door itself.

FIG. 10 illustrates door 14 fully closed. Door coupling element 20 couples between cartridge coupling element 16 of the cartridge and coupling element 22 of the activation mechanism, so that the activation mechanism can now cause the substance contained in the cartridge to be metered out of the cartridge for eventual administration to the patient.

Figure 11:
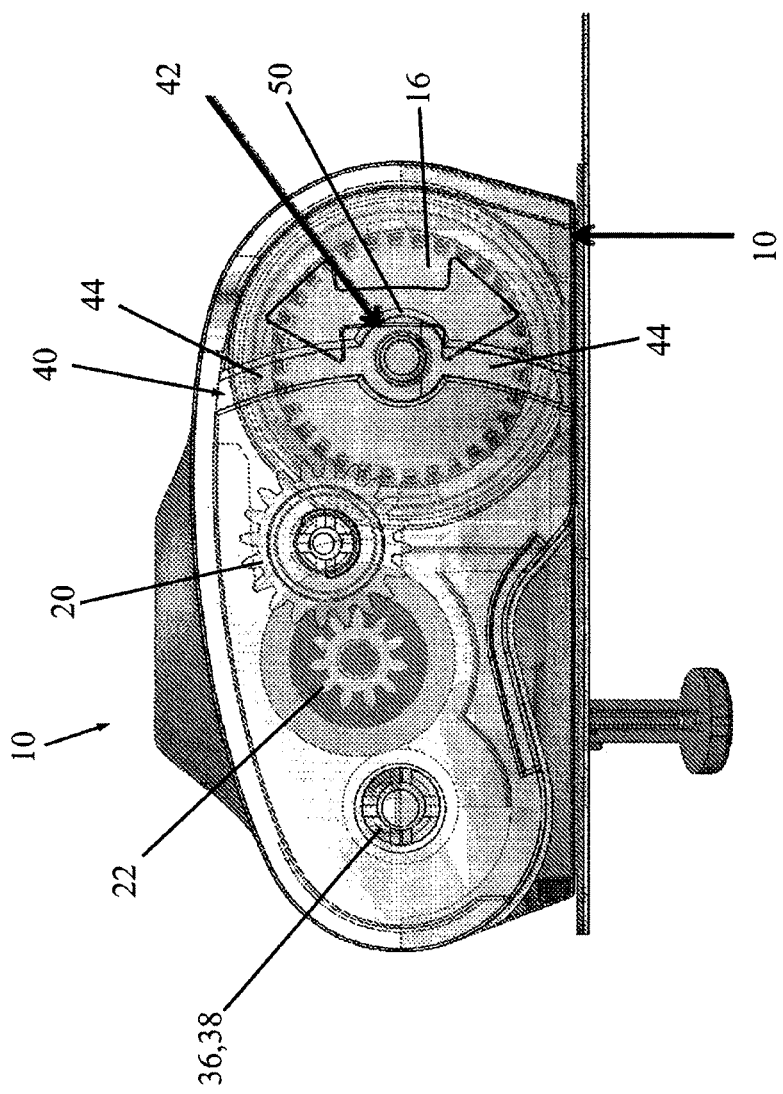
FIG. 11 is a simplified illustration of the door fully closed, showing a snap that snaps the door to the body of the apparatus.

Reference is now made to FIG. 11. When door 14 is fully closed, hub 42 of closure member 40 snaps and is fixedly received in a snap member 50 (curved snap member) so that door 14 is properly secured to the body of apparatus 10.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

I claim:

1. A method of loading a cartridge containing a substance to be administered to a subject into an apparatus for administering the substance, the method comprising:

moving a door of the apparatus into an open position thereof to expose a pathway within the apparatus;

inserting the cartridge into the pathway, the cartridge comprising a cartridge coupling element and a septum at an end opposite to the cartridge coupling element, the cartridge coupling element being connectable to a coupling element of an activation mechanism disposed in the apparatus and operative to cause the substance in the cartridge to be metered out; and moving the door to a closed position, which couples a door coupling element with each of the cartridge coupling element and the activation mechanism coupling element, thereby coupling the cartridge coupling element with the activation mechanism coupling element.

2. The method of claim 1, wherein the inserting step further comprises abutting the cartridge against a cartridge stopper disposed in the apparatus when the cartridge is inserted into the pathway.

3. The method of claim 1, wherein the apparatus comprises a hollow needle disposed therein, and further comprising a step of puncturing the septum with the needle when the cartridge is inserted into the pathway.

4. The method of claim 1, wherein the door further comprises at least one rib and the apparatus further comprises a corresponding at least one groove, wherein the step of moving the door into the closed position includes inserting the at least one rib in the corresponding at least one groove.

5. The method of claim 1, wherein the door further comprises a closure member on an inside surface thereof, the closure member comprising a hub, wherein the step of moving the door into the closed position includes fixedly inserting the hub into a snap member of the apparatus.

6. The method of claim 1, wherein the apparatus further comprises a surface configured to adhere to skin of the subject.

7. A method of loading a cartridge containing a substance to be administered to a subject into an apparatus for administering the substance, the method comprising:
    moving a door of the apparatus into an open position thereof to expose a pathway within the apparatus;
    inserting the cartridge into the pathway, the cartridge comprising a cartridge coupling element connectable to a coupling element of an activation mechanism disposed in the apparatus and operative to cause the substance in the cartridge to be metered out; and
    moving the door to a closed position, wherein a door coupling element couples the cartridge coupling element with the activation mechanism coupling element,
    wherein the apparatus further comprises a locking latch cantilevered from a base thereof and the cartridge further comprises a rim proximate a rear end thereof, and wherein the inserting step further comprises depressing and sliding over and past the locking latch with the rim of the cartridge during insertion of the cartridge into the pathway whereby when the rim slides past the locking latch, the locking latch springs back and abuts against the rim, locking the cartridge into the pathway.

8. A method of loading a cartridge containing a substance to be administered to a subject into an apparatus for administering the substance, the method comprising:
    moving a door of the apparatus into an open position thereof to expose a pathway within the apparatus;
    inserting the cartridge into the pathway, the cartridge comprising a cartridge coupling element connectable to a coupling element of an activation mechanism disposed in the apparatus and operative to cause the substance in the cartridge to be metered out; and
    moving the door to a closed position, wherein a door coupling element couples the cartridge coupling element with the activation mechanism coupling element,
    wherein the door further comprises a closure member on an inside surface thereof, the closure member comprising at least one inclined ramp member, and wherein the step of moving the door into the closed position thereof includes sliding the at least one ramp member against the cartridge coupling element, pushing the cartridge into the apparatus.

9. A method of loading a cartridge containing a substance to be administered to a subject into an apparatus for administering the substance, the method comprising:
    moving a door of the apparatus into an open position thereof to expose a pathway within the apparatus;
    inserting the cartridge into the pathway, the cartridge comprising a cartridge coupling element connectable to a coupling element of an activation mechanism disposed in the apparatus and operative to cause the substance in the cartridge to be metered out; and
    moving the door to a closed position, wherein a door coupling element couples the cartridge coupling element with the activation mechanism coupling element,
    wherein the cartridge coupling element, the door coupling element, and the activation mechanism coupling element comprise gears.

10. A method of loading a cartridge containing a substance to be administered to a subject into an apparatus for administering the substance, the method comprising:
    moving a door of the apparatus into an open position thereof to expose a pathway within the apparatus;
    inserting the cartridge into the pathway, the cartridge comprising a cartridge coupling element connectable to a coupling element of an activation mechanism disposed in the apparatus and operative to cause the substance in the cartridge to be metered out; and
    moving the door to a closed position, which couples a door coupling element with each of the cartridge coupling element and the activation mechanism coupling element, thereby coupling the cartridge coupling element with the activation mechanism coupling element, wherein the door coupling element is sized and shaped to transmit rotary motion.

11. A method of loading a cartridge containing a substance to be administered to a subject into an apparatus for administering the substance, the method comprising:
    moving a door of the apparatus into an open position thereof to expose a pathway within the apparatus;
    inserting the cartridge into the pathway until a shoulder of the cartridge abuts against a cartridge stopper disposed in the apparatus, the cartridge comprising a cartridge coupling element connectable to a coupling element of an activation mechanism disposed in the apparatus and operative to cause the substance in the cartridge to be metered out; and
    moving the door to a closed position, which couples a door coupling element with each of the cartridge coupling element and the activation mechanism coupling element, thereby coupling the cartridge coupling element with the activation mechanism coupling element.

* * * * *